(12) United States Patent
Svensson et al.

(10) Patent No.: US 6,945,968 B2
(45) Date of Patent: Sep. 20, 2005

(54) FASTENING SYSTEM FOR AN ABSORBENT PRODUCT

(75) Inventors: Charlotth Svensson, Stenungsund (SE); Anna Svernlöv, Kullavik (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/995,585

(22) Filed: Nov. 29, 2001

(65) Prior Publication Data

US 2002/0065504 A1 May 30, 2002

Related U.S. Application Data

(60) Provisional application No. 60/253,754, filed on Nov. 29, 2000.

(51) Int. Cl.[7] .............................................. A61F 13/15
(52) U.S. Cl. ...................................... 604/389; 604/391
(58) Field of Search ................................ 604/386, 387, 604/389–391

(56) References Cited

U.S. PATENT DOCUMENTS

| | | | |
|---|---|---|---|
| 5,399,219 A | | 3/1995 | Roessler et al. |
| 5,653,704 A | | 8/1997 | Buell et al. |
| 5,865,825 A | | 2/1999 | Schlinz |
| 5,897,546 A | * | 4/1999 | Kido et al. .................. 604/391 |
| 5,984,911 A | * | 11/1999 | Siebers et al. .............. 604/391 |
| 6,102,901 A | * | 8/2000 | Lord et al. .................. 604/386 |
| 6,306,121 B1 | * | 10/2001 | Damaghi et al. ...... 604/385.03 |
| 6,406,466 B1 | * | 6/2002 | Pozniak et al. ............. 604/386 |
| 6,613,032 B2 | * | 9/2003 | Ronnberg et al. ...... 604/385.03 |

FOREIGN PATENT DOCUMENTS

| | | |
|---|---|---|
| EP | 240213 | 10/1987 |
| EP | 0 858 787 A1 | 8/1998 |
| EP | 1084687 | 3/2001 |
| WO | WO 97/36566 A1 | 10/1997 |

* cited by examiner

*Primary Examiner*—Larry I. Schwartz
*Assistant Examiner*—C. Lynne Anderson
(74) *Attorney, Agent, or Firm*—Burns, Doane, Swecker & Mathis, L.L.P.

(57) ABSTRACT

The invention relates to an absorbent product, such as a diaper or an incontinence garment, comprising a casing, an outer side of the casing being distal from the body of the wearer in use of the garment and an inner side being proximal to the body of the wearer in use of the garment, said casing having a front part, a rear part and a crotch part lying between the front and rear parts, the casing comprising an absorbent structure, whereby the absorbent product further comprises a fastening system, for attaching opposing side portions of the front and rear parts to each other, comprising at least two cooperating fastening elements, wherein the first element functions as a landing zone for the second element, characterized in that the first element comprises at least one skewing-preventing part, which skewing-preventing part prevents the front and rear parts to slide relative one another, as it adheres to the inner part.

10 Claims, 3 Drawing Sheets

FASTENING SYSTEM FOR AN ABSORBENT PRODUCT

This application claims priority under 35 U.S.C. §§119 and/or 365 to Provisional Application No. 60/253,754, filed in the United States on Nov. 29, 2000; the entire content of which is hereby incorporated by reference.

TECHNICAL FIELD

The invention relates to an absorbent product, such as a diaper or an incontinence garment, comprising a casing, an outer side of the casing, being distal from the body of the wearer in use of the garment, and an inner side being proximal to the body of the wearer in use of the garment, said casing having a front part, a rear part and a crotch part lying between the front and rear parts, and a fastening system, for attaching opposing side portions of the front and rear parts to each other, comprising at least two co-operating fastening elements, wherein the first element functions as a landing zone for the second element.

BACKGROUND OF THE INVENTION

The fastening system of a diaper is supposed to connect the front and rear parts of the diaper in a way that provides a good fit on the wearer. A good fit is important for the function of the diaper, especially for preventing leakage to occur. A problem during use is that the front and rear parts may slide relative each other. Specifically, the ears of the front part (or of the rear part, depending on the choice of construction) of the diaper may slide in relation to each other, which gives rise to sore and bad fit, which in turn may lead to leakage.

EP-A-0240213 discloses an absorbent product having flexible leg openings aiming to solve the problem of sliding of the front and rear parts relative to each other during use. This is solved with an outer and an inner fastening means. The inner means is said to prevent disposition of the overlapping parts in the rear and front parts, and it may be integrated with the front and rear part, respectively. The fastening can be performed in several ways. The outer fastening means is an adhesive tape, extending from the ear of the rear part.

Thus, EP-A-0240213 discloses a solution for preventing the sliding of the front and rear parts relative one another. However, the manufacturing of this fastening system is rather complex, compared to normal fastening systems. Accordingly, there is a need for a fastening system providing the skewing-preventing feature, while still being easy to manufacture.

Thus, one main object of the invention is to provide an absorbent product fulfilling that need.

SUMMARY OF THE INVENTION

The object of the invention is accomplished by an absorbent product, such as a diaper or an incontinence garment, comprising a casing, an outer side of the casing being distal from the body of the wearer in use of the garment and an inner side being proximal to the body of the wearer in use of the garment, said casing having a front part, a rear part and a crotch part lying between the front and rear parts, and a fastening system, for attaching opposing side portions of the front and rear parts to each other, comprising at least two co-operating fastening elements, wherein the first element functions as a landing zone for the second element, characterised in that the first element comprises at least one skewing-preventing part.

The advantage with an absorbent product as described above is among others that it is easy to manufacture, while the first element is provided as one item, and that it gives a fastening system that provides a great flexibility in the side portions. The skewing preventing effect is thereby accomplished with a separate element.

As one preferred embodiment an absorbent product is provided, wherein the first element comprises a landing zone, surrounded by skewing-preventing parts on its two lateral sides.

In this way a practical solution that is easy to manufacture is provided, as one first element is provided for both second elements on the opposite side of the casing. The second element on both ears can adhere to the landing zone, whereby the skewing-preventing parts may adhere to the inner side of each ear or tab, which for example is made of non-woven. Accordingly, sliding is prevented.

Yet another embodiment is an absorbent product, wherein the first element in divided into two separate pieces, each piece comprising a landing zone and a skewing preventing part, where said skewing preventing part is positioned laterally outside the landing zone.

Hereby, one first element is provided for each second element on the opposite side of the casing.

Still another embodiment is an absorbent product, wherein the skewing-preventing part of the first element is positioned at a distance from the side edge of the side portion, on which it is attached, of 0–120 mm, in order to secure the skew-preventing mechanism.

In another embodiment, the skewing-preventing part lies outside the lateral side of the casing in the front end. This is especially beneficial when absorbent products are used, that have side portions (ears) being small.

One preferred embodiment is an absorbent product as defined above, wherein the skewing-preventing part is a hook material part capable to adhere to the inner side of the casing.

In this way sliding is readily prevented, as a suitable hook connection provides a good binding to many common materials.

Furthermore, in another aspect, the landing zone comprises loop material, thereby providing a good connection with the second fastening element.

According to yet another embodiment, the skewing preventing part is capable to adhere to the backing sheet material of the side edges of the part to which the second element is attached, thereby holding together an absorbent product being folded in the crotch part. Accordingly, the skewing-preventing parts can be used to keep the product folded before or after use.

Moreover, yet another advantage with the solution according to the invention lies in its construction. As the landing zone and the hook part of the first element are integrated in one single piece, the fastening system of the invention is easy to apply to the absorbent product.

DETAILED DESCRIPTION OF THE INVENTION

By "skewing-preventing part" is meant a part that prevents the side portions of the rear and front parts of a sanitary product to slide or move relative one another, in the applied state of the product. The skewing preventing part adheres to the part (rear or front) that is opposite to the one it is applied to, thereby preventing sliding between the overlapping side portions of the front and rear parts.

Figure 1:
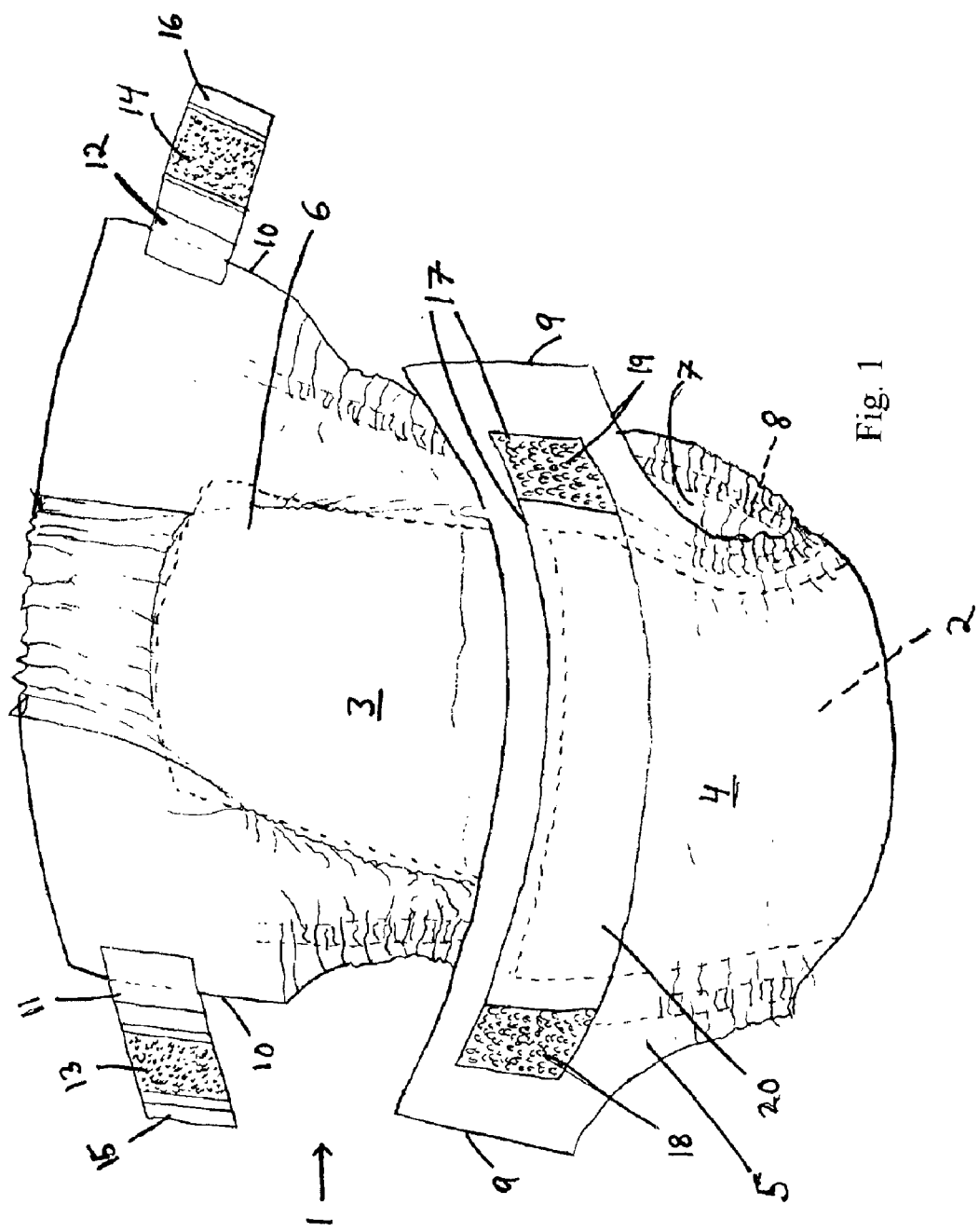
FIG. 1 shows in a perspective view an absorbent product according to a first embodiment of the invention.

FIG. 1 discloses a diaper 1. As is conventional in this field of the art, the diaper comprises an absorbent body 2, being enclosed between a liquid-permeable top sheet 3 and a liquid-impermeable backing sheet 4, these sheets being fastened to each other in portions thereof reaching beyond the absorbent body. The diaper has a front part 5, a rear part 6 and an intermediate crotch part 7, the longitudinal direction of the diaper extending from the rear to the front edge thereof. The diaper also comprises leg elastics 8, for example one or several elastic threads or bands disposed between the top sheet and the backing sheet along the sides of the diaper, at least in the crotch part thereof, and attached to the top sheet and/or backing sheet in a stretched state. The top sheet 3 and the backing sheet 4 constitutes a casing for the absorbent body 2 and the side portions of the front 5 and rear part 6 of the diaper 1 are laterally projecting from the front and rear parts in relation to the extension of the casing in the crotch part 7 of the diaper. The side portions are limited by lateral side edges 9 and 10 of the front and rear part, respectively.

According to the invention, the side portions, or ears, extend laterally to the sides from the rear part 6 and front part 5. On the front part a first fastening element 17 is attached, having a landing zone 20 and two skewing preventing parts 18 and 19, wherein the element 17 extends laterally over the waist area of the front part 5 of the diaper 1, from the first ear to the other. On the ears of the rear part 6 two tabs 11 and 12 are attached, on which two second fastening elements 13 and 14 are attached, which are constructed to be able to adhere to the first fastening element 17. The fastening elements (13, 14 and 17) attaches opposing side-portions of the front and rear parts to each other in order to give the diaper a pants-like configuration. The first 17 and second fastening elements 13 and 14 may also be attached in the reversed order to the rear and front parts, respectively. The skewing preventing parts 18 and 19 adheres to the inner side of the opposing side portion, in order to prevent the front and rear parts to slide relative one another.

The absorbent product may for example be of a "hour-glass"-shape, wherein the "ears" of the time-glass constitutes the side portions of the absorbent product. The fastening element functioning as a landing zone 17 is then applied close to the waist-line of the outer side of either the front or rear part of the product. The other element (13, 14) is preferably applied to a fastener tab (11, 12) of the absorbent product attached close to the waist-line of either the rear or the front part of the product. Outside the element (13, 14), a grip tab (15, 16) is provided, in order to be gripped by hand when adjusting the fastening system.

In this embodiment the landing zone 20 of the first fastening element 17 is a loop landing zone and the skewing preventing parts 18 and 19 is made of hook material. The second fastening elements 13 and 14 are made of a hook material. Preferably the area of the first fastening element is larger than the area of the second fastening elements, in order to give a possibility to adjust the length of the waistline of the diaper when applied on a wearer. The extension of the first fastening element 17 in the side portions of the front part of the diaper is such, that when the second fastening elements 13 and 14 are attached to the respective outer end of the landing zone 20 of the first fastening element 17, the opposing side portions of the rear and front parts of the diaper are slightly overlapping.

The liquid-permeable top sheet 3 is made of a soft skin-friendly material. Examples of suitable materials are different types of non-woven. Other material that can be used are perforated plastic films, plastic nets or knitted, crotched or woven textile materials or combinations and laminates of the above mentioned types of material. The plastic material can be a thermoplastic material, for example polyethylene (PE). The non-woven material can be formed of natural fibres, such as cellulose or cotton fibres, but can alternatively consist of synthetic fibres, such as PE, polypropylene (PP), polyurethane (PU), a polyester, nylon or regenerated cellulose, or a mix of different fibres. All materials used for top sheets in absorbent sanitary garments can be used for the top sheet 3 and the above mentioned materials are only given as examples.

The liquid-impermeable backing sheet 4 consists of a flexible material, preferably a thin plastic film of PE, PP or a polyester but could also consist of a laminate of a liquid-permeable material, such as a non-woven, and a liquid-impermeable material, such as e.g. a plastic film. All materials that are used for liquid-impermeable backing sheets are conceivable. The backing sheet can advantageously be air-permeable.

The absorbent body 2 is preferably formed of cellulose fibres but also other natural materials, such as cotton fibres or peat can be used. Alternatively can absorbent synthetic fibres or a mixture of natural and synthetic fibres be used. The absorbent body can also comprise a super-absorbent, i.e. a polymer having the capacity to absorb liquid to an amount several times larger than its own weight. The absorbent body can also contain form stabilising and/or liquid dispersing components and also bonding agents for holding together short fibres and particles to a continuous unit. Furthermore, the absorbent body can contain more than one layer of absorbent material.

Figure 2:
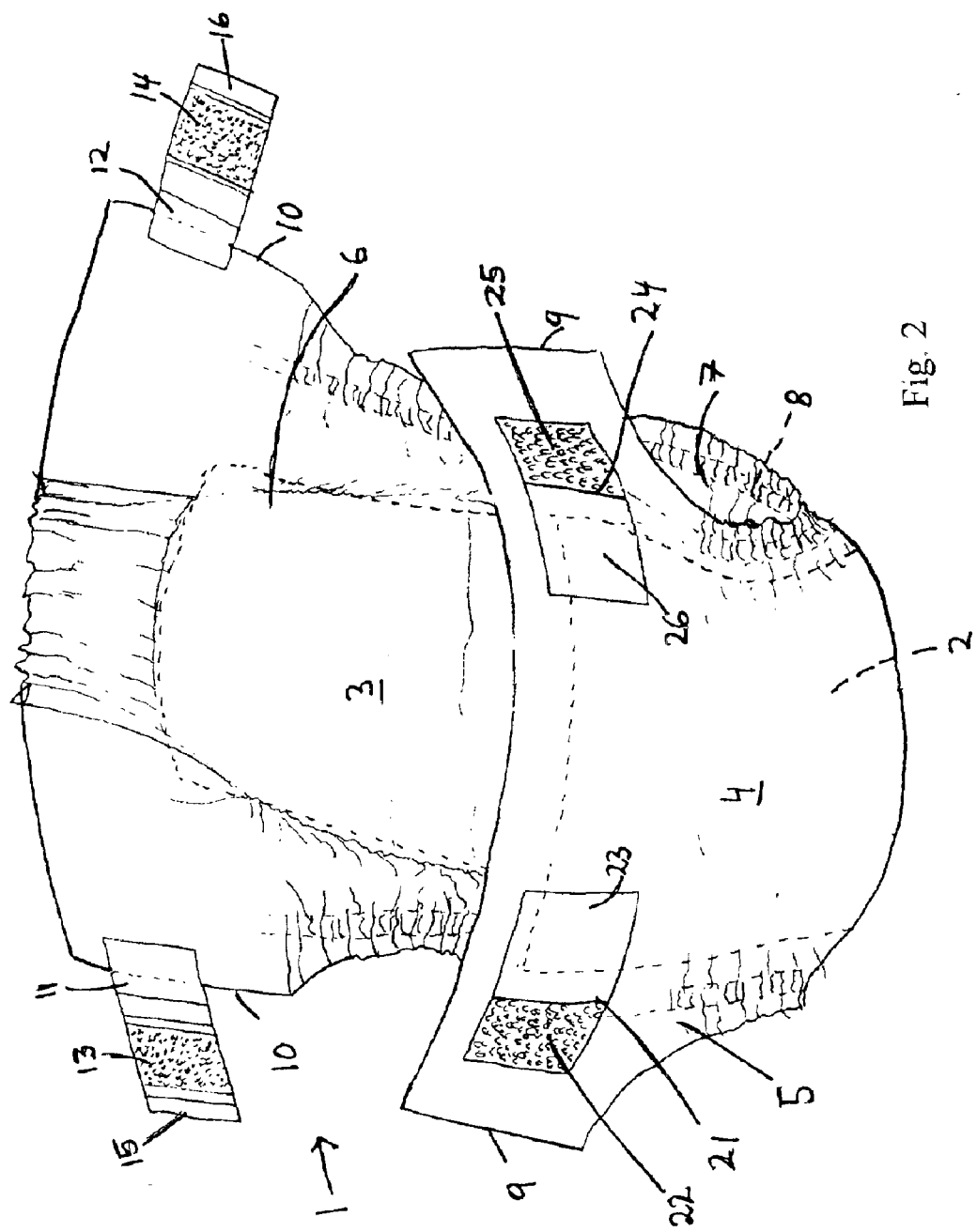
FIG. 2 shows in a view similar to FIG. 1 an absorbent product according to a second embodiment of the invention.

According to a second embodiment (FIG. 2) the first fastening element is divided in two separate pieces 21 and 24, where each one is attached to the left and right ear, respectively, of the front part. Each piece of the first fastening element 21 and 24 comprises a landing zone 23 and 26 and a skewing preventing part 22 and 25, where the skewing preventing part is positioned towards the outer part of the side portions. The function is essentially the same as for the first described embodiment. The first and second fastening elements may also be attached in the reversed order to the rear and front part of the diaper, respectively.

According to yet another embodiment (not shown) the first fastening element comprises only a skewing preventing part, and the material of the outer side of the backing sheet 4 in the front part (or of the rear part) functions as a landing zone for the second element.

Figure 3:
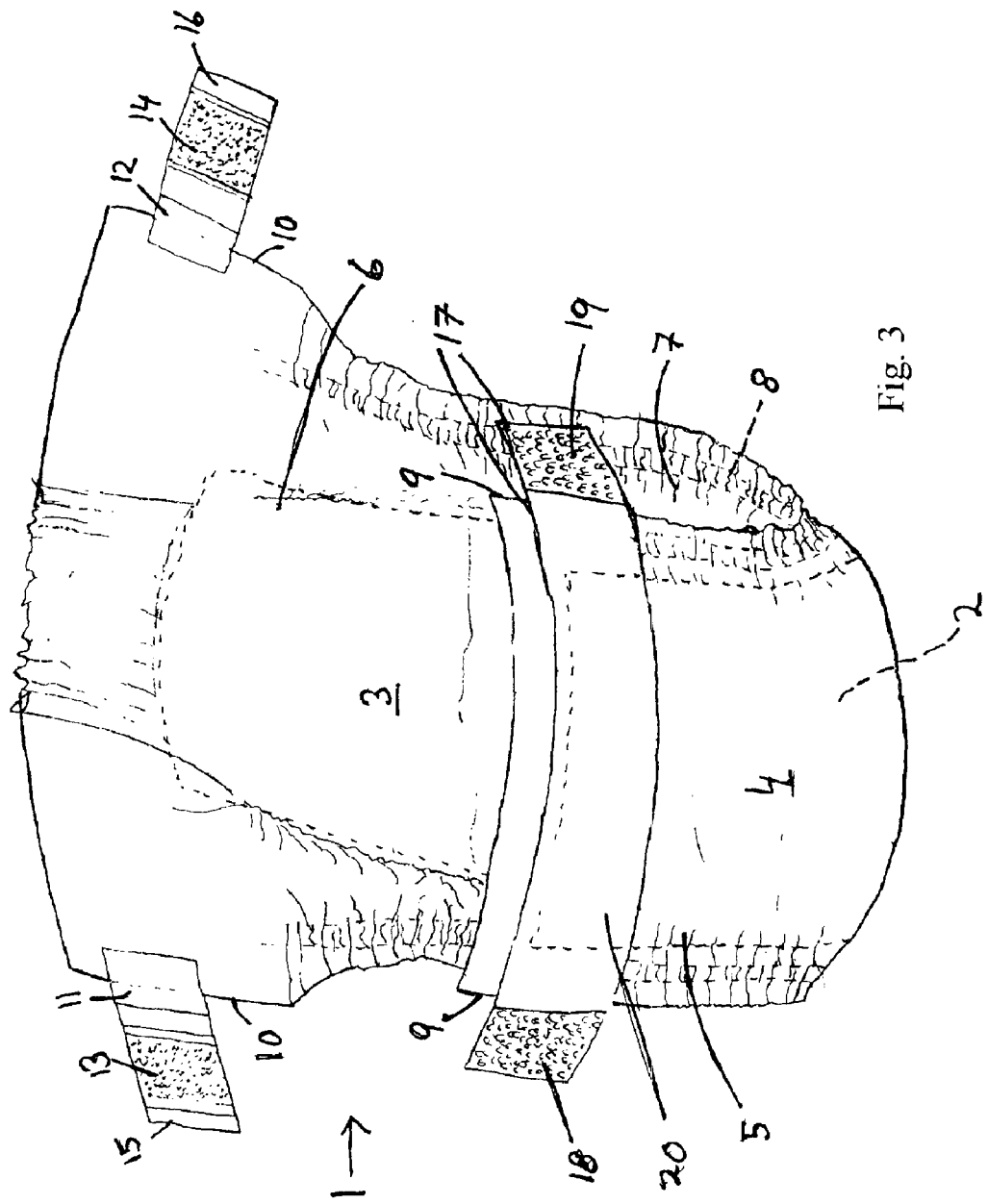
FIG. 3 shows an embodiment of the invention in which the skewing preventing parts are positioned outside the lateral side edges of the absorbent product.

FIG. 3 shows still another embodiment of the invention, wherein the skewing preventing part of the first fastening element extends outside the lateral side edges (9) of the side portion to which it is attached. The absorbent product showed in this figure is analogue to the product showed in FIG. 1, with the difference that distance between the lateral side edges of the front part (9) is smaller in the absorbent product of FIG. 3. The function is mainly the same as for the embodiments discussed above.

The purpose of providing a skewing-preventing part (18, 19, 22, 25) according to the invention is that it prevents the front and rear parts from sliding relative one another, and that it also is easy to apply the first element (17, 21, 24), comprising the skewing-preventing part, to the absorbent product, as the skewing-preventing part and the landing zone are provided as one element. In fact, existing applicator devices can be used making the manufacture as easy as the application of a first element without the skewing-preventing part.

Preferably, the skewing-preventing part is made of hook-material capable to adhere to the inner side of the casing. It may also be made of any other type of material that can prevent sliding of the rear and front parts relative one another. Such a material should provide a high friction coefficient together with the opposite side of the inner side of the casing. As such materials may a polymer or plastics material be used, optionally equipped with embossements, or having a rough surface.

The fastening system is preferably of hook and loop type, but it may also comprise a tape and a tape landing zone, as well as any other suitable system.

In all cases, the skewing-preventing part is positioned so as to co-operate with the inner side of the front or rear part or with the fastener tab.

In a preferred embodiment, the skewing-preventing part is made of hook material, and the inner side of the ear is made of non-woven. A loop-landing zone with hook-elements on its sides is applied to the outer side of the front part, with the purpose for the hook elements to hook to the NW-inner side of the rear part, and thereby preventing the diaper from sliding.

One further advantage with the invention is that the skewing-preventing parts are positioned in the "tape-line", which increases the chances for the hook-elements to hook to the NW-inner side of "the ears".

In yet another embodiment, the skewing preventing part is capable to adhere to the backing sheet material of the part to which the second element is attached. This makes it possible to hold an absorbent product, which is folded in the crotch part, together before or after use. This is especially well accomplished when the backing sheet has a textile surface and the skewing preventing part is of hook material.

Further, the skewing-preventing part could be positioned right above the end of the leg-elastics, in order to contribute to its stretch.

The description illustrates how the invention may be performed. However, the description is not intended to limit the scope of the invention, and modifications of the exemplified embodiments are fully possible. For example, the two elements of the fastening system may both be applied to the front part as well as to the rear part. Further, the absorbent product may be of different kinds, such as diapers and incontinence garments. The construction of the absorbent product may include an absorbent product, or may provide for an insert. The element of the fastening system, which adheres to the landing zone part, may also be attached to the inside of the ears, instead of the fastener tab.

What is claimed is:

1. An absorbent product comprising:
   a casing, an outer side of the casing being distal from a body of a wearer of the product in use and an inner side of the casing being proximal to the body of the wearer of the product in use, said casing having a front part, a rear part, a crotch part lying between the front part and rear part, and an absorbent structure; and
   a fastening system for attaching opposing side portions of the front part and the rear part to each other;
   the fastening system comprising at least two cooperating fastening elements, wherein a first of the elements functions as a landing zone for a second of the elements, and the first of the elements is attached to the front part of the casing;
   and the first element comprises at least one skewing-preventing part, wherein the at least one skewing-preventing part is adapted to adhere to the rear part of the casing; and
   the at least one skewing-preventing part is positioned in line with the landing zone as viewed in the lateral direction of the absorbent product.

2. The absorbent product according to claim 1, wherein the first element is divided into two separate pieces, each piece comprising a landing zone and a skewing-preventing part, wherein said-skewing-preventing part of each piece is positioned laterally outside the landing zone.

3. The absorbent product according to claim 1, wherein the skewing-preventing part of the first element is positioned at a distance of 0–120 mm from a lateral side edge of the side portion on which it is attached.

4. An absorbent product comprising:
   a casing, an outer side of the casing being distal from a body of a wearer of the product in use and an inner side of the casing being proximal to the body of the wearer of the product in use, said casing having a front part, a rear part, a crotch part lying between the front part and rear part, and an absorbent structure; and
   a fastening system for attaching opposing side portions of the front part and the rear part to each other;
   the fastening system comprising at least two cooperating fastening elements, wherein a first of the elements functions as a landing zone for a second of the elements, and the first of the elements is attached to the front part of the casing;
   and the first element comprises at least one skewing-preventing part, wherein the at least one skewing-preventing part is adapted to adhere to the rear part of the casing; and
   wherein the skewing-preventing part is positioned at least partly outside a lateral side of the casing in the front part.

5. The absorbent product according to claim 1, wherein the skewing-preventing part is a hook material part capable of adhering to the inner side of the casing.

6. The absorbent product according to claim 1, wherein the landing zone comprises a loop material.

7. The absorbent product according to claim 1, wherein the second element comprises a hook material.

8. The absorbent product according to claim 1, wherein the skewing-preventing part is capable of adhering to a backing sheet material of side edges to which the second element is attached.

9. The absorbent product of claim 1, wherein the absorbent product is a diaper or an incontinence garment.

10. The absorbent product of claim 1, wherein the first element comprises a landing zone having two lateral sides and a skewing-preventing part on each of the two lateral sides.

* * * * *